United States Patent
Hunter et al.

(10) Patent No.: US 9,707,317 B2
(45) Date of Patent: Jul. 18, 2017

(54) PULSED CURRENT SINTERING FOR SURFACES OF MEDICAL IMPLANTS

(75) Inventors: Gordon Hunter, Memphis, TN (US); Vivek Pawar, Germantown, TN (US); Daniel A. Heuer, Memphis, TN (US); Abraham Salehi, Bartlett, TN (US); Michael B. Cooper, Nesbit, MS (US)

(73) Assignee: Smith & Nephew, Inc., Memphis, TN (US)

( * ) Notice: Subject to any disclaimer, the term of this patent is extended or adjusted under 35 U.S.C. 154(b) by 780 days.

(21) Appl. No.: 13/488,323

(22) Filed: Jun. 4, 2012

(65) Prior Publication Data

US 2012/0245697 A1 Sep. 27, 2012

Related U.S. Application Data

(63) Continuation of application No. 11/183,456, filed on Jul. 18, 2005, now abandoned.

(60) Provisional application No. 60/589,143, filed on Jul. 19, 2004.

(51) Int. Cl.
| | |
|---|---|
| *A61L 27/30* | (2006.01) |
| *A61L 27/56* | (2006.01) |
| *B22F 3/105* | (2006.01) |
| *B22F 7/08* | (2006.01) |
| *A61F 2/28* | (2006.01) |
| *A61F 2/30* | (2006.01) |

(52) U.S. Cl.
CPC ............ *A61L 27/30* (2013.01); *A61L 27/56* (2013.01); *B22F 3/105* (2013.01); *B22F 7/08* (2013.01); *A61F 2002/2817* (2013.01); *A61F 2002/30677* (2013.01); *A61F 2002/30957* (2013.01); *A61F 2002/30968* (2013.01); *A61F 2310/00293* (2013.01); *B22F 2998/00* (2013.01)

(58) Field of Classification Search
CPC ..................... A61L 27/30; A61F 2002/2817
USPC ..................................... 427/2.26
See application file for complete search history.

(56) References Cited

U.S. PATENT DOCUMENTS

| | | | |
|---|---|---|---|
| 5,734,959 A | * | 3/1998 | Krebs et al. ........... 419/2 |
| 7,208,222 B2 | * | 4/2007 | Rolfe et al. ........... 428/304.4 |

FOREIGN PATENT DOCUMENTS

| | | | |
|---|---|---|---|
| JP | 11035379 A | * | 2/1999 |
| JP | H11-025979 | | 2/1999 |
| JP | 2003268410 | | 9/2003 |

OTHER PUBLICATIONS

Japanese Office Action with English translation.
Japanese Patent Office, Japanese Second Office Action, dated Jul. 2, 2013, 5 pages.

* cited by examiner

*Primary Examiner* — Weiping Zhu
(74) *Attorney, Agent, or Firm* — David Chambers

(57) ABSTRACT

A porous medical implant and a method of making same is described. The medical implant comprises a porous surface formed by application of pulsed electrical energy ins such a way as to cause a localized heating in the surface of the material comprising portions of the implant. The method comprises a pulsed current sintering technique.

53 Claims, 2 Drawing Sheets

PULSED CURRENT SINTERING FOR SURFACES OF MEDICAL IMPLANTS

CROSS-REFERENCE TO RELATED APPLICATIONS

This is a continuation of U.S. application Ser. No. 11/183,456, filed Jul. 18, 2005, entitled "PULSED CURRENT SINTERING FOR SURFACES OF MEDICAL IMPLANTS" which claims priority to U.S. provisional application Ser. No. 60/589,143, filed on Jul. 19, 2004.

TECHNICAL FIELD

The present invention is directed toward the fabrication of a porous sintered surface for medical implants.

BACKGROUND OF THE INVENTION

For a variety of reasons, it is sometimes necessary to surgically correct an earlier implanted medical implant (most commonly a prosthetic joint) or replace it with an entirely new medical implant. Typically, this results from either a loosening of the implant in the implant site, or the deterioration of the implant due to forces such as abrasion. Ideally, an medical implant is often formed from a high-strength material which is not only able to accommodate the various loading conditions that it may encounter, but is also non-toxic to, and otherwise biocompatible with, the human body. It is also preferable to implant the device in such a way as to enhance fixation over the long term.

A number of advances have been made to increase service life of medical implants by increasing their resistance to forces such as abrasion. The advent of oxidized zirconium, first described by Davidson in U.S. Pat. No. 5,037,438 has provided a surface with superior hardness which is also resistance to brittle fracture, galling, fretting and attack by bodily fluids. A similar advance in the area of fixation stability will address the other major source of implant failure and would represent a significant advance in implant service life.

In cases of extreme loading conditions as is often the case for artificial hips, prosthetic joints may be made from metal alloys such as titanium, zirconium, or cobalt chrome alloys. Not only are these metal alloys of sufficient strength to withstand relatively extreme loading conditions, but due to their metallic nature, a metallic porous coating typically of titanium or cobalt chrome may be secured to the metal alloy by a metallic bond. Such metallic porous coatings are useful for providing initial fixation of the implant immediately after surgery, but also serve to facilitate long-termstability by enhancing bone ingrowth and on growth.

While medical implant devices made from biocompatible metal alloys are effective, they may lack certain desirable characteristics. For example, metal alloys have poor flexibility and therefore do not tend to distribute load as evenly as would be desired. Uneven loads tend to result in a gradual loosening of the implant. As such loosening becomes more severe, revision or replacement becomes necessary. For this reason, it is desirable to design medical implants generally and prosthetic joints specifically in such a way as to improve their in vivo fixation stability.

One way this problem has historically been addressed in the past is through the use of modified surfaces for medical implants which increase surface contact area and promote bone ingrowth and ongrowth. Another more recent technique involves the use of depositing material onto the surface of an implant, the material being the emission of a plasma spray source. This is discussed in U.S. Pat. Nos. 5,807,407, 6,087,553, and 6,582,470, among others, which are incorporated by reference as though fully disclosed herein.

A promising way to form porous products involves fusing materials in such as way as to effect a porous finished material. Such approaches have been the subject of past work. Electrical discharge is one mechanism by which this has been performed, as in U.S. Pat. Nos. 5,294,769, 5,352,385, and 5,421,943. Sintered materials have also been the subject of investigation as a potential solution to the issue of fixation stability improvement through the use of porous materials which allow for tissue ingrowth and ongrowth. For example, Chowdhary in U.S. Pat. No. 5,104,410, describes a prosthesis having a metallic substrate and multiple sintered layers. The sintered layers were firmed by conventional methods of sintering, using temperatures of 1100° C. for one hour at $10^{-5}$-$10^{-6}$ torr. While such sintered surface imparts desirable porosity, sintering at such extreme conditions of temperature and time fundamentally alter the nature of the substrate in undesirable ways.

BRIEF SUMMARY OF THE INVENTION

A porous medical implant and a method of making same is described. The medical implant comprises a porous surface formed by application of pulsed electrical energy in such a way as to cause a localized heating in the surface of the material comprising portions of the implant.

In one aspect of the present invention, there is a method of making a medical implant having a porous surface and a solid substrate, comprising the steps of placing a finite number of individual bodies in continuous contact with one another, the finite number of individual bodies comprising a first material; sintering the first material by applying pulsed electrical energy across at least a portion of the aggregate mass of the individual bodies, thereby creating a cohesive porous structure and, attaching the first material to a second material, the second material comprising the solid substrate. In some embodiments, the step of attaching said first material to a second material comprises sintering said first material to said second material by applying pulsed electrical energy across at least a portion of the aggregate mass of the first material and the second material while the first material and the second material are in physical contact with one another. In some embodiments, the steps of sintering and attaching are performed simultaneously by applying pulsed electrical energy across at least a portion of the aggregate mass of the first material and the second material while the first material and the second material are in physical contact with one another. In some embodiments, the steps of sintering and attaching are performed sequentially by first applying pulsed electrical energy across at least a portion of the aggregate mass of the first material and thereafter applying pulsed electrical energy across at least a portion of the aggregate mass of the first material and the second material while the first material and the second material are in physical contact with one another. In some embodiments, the step of attaching said first material to a second material comprises a step selected from the group consisting of welding, soldering, diffusion bonding, brazing, adhering using an adhesive or grouting material or both, and any combination thereof. In some embodiments, the step of placing a finite number of individual bodies in continuous contact with one another comprises placing a finite number of individual bodies of at least two materials in continuous contact with one another. The method may further comprise the step of removing at least a portion of at least one of said at least two materials either daring or after said step of sintering, thereby creating a cohesive porous structure where said material was removed. Preferably, the method further comprises the step of applying a mechanical, load to at least a portion of said first material or to at least a portion of said second material or to at least a portion of both said first material and said second material. In cases where a mechanical load is applied, it is preferably applied during said step of sintering. In some embodiments, the step of sintering is performed at an elevated temperature. In some embodiments, the step of sintering comprises applying pulsed electrical energy at high frequencies. In some embodiments, the first material and said second material are selected from the group consisting of metal, ceramic, polymer, composite materials, and any combination thereof. The first material and second material may or may not be different. Preferably the first material and the second material are refractory materials. Alternatively, one or both of the first material and the second material may be non-refractory materials. In some embodiments, a portion of the individual bodies of the first material are of different composition from another portion of the individual bodies of the first material. Accordingly in some embodiments, a portion of the individual bodies of the first material comprises a refractory material and another portion of the individual bodies of the first material comprises a non-refractory material. In some embodiments, one of the first material and the second material is refractory and the other is non-refractory. In some embodiments, the first material has a form selected from the group consisting of symmetric particles, asymmetric particles, single fibers, multiple fibers, flat porous sheets, deformed porous sheets, reticulated open-celled structures, and any combination thereof. In some embodiments, the first material has a symmetric particle form and is a spherical particle. In sonic embodiments, the sintering step is performed in a controlled environment. The controlled environment may be one having a pressure less than atmospheric pressure. The controlled environment may be one comprising an atmosphere of an inert gas. The controlled environment may be one comprising an atmosphere of a reactive gas. In some embodiments of the method, the controlled environment is varied during the step of sintering. In some embodiments of the method, the step of placing comprises using a binder. In some embodiments, the method further comprises the step of infusing at least a portion of the porous region with a material. In some embodiments where an infusing step is used, the step of infusing comprises infusing with a method selected from the group consisting of direct compression molding, injection, solution deposition, vapor deposition, and any combination thereof. In some embodiments where an infusing step is used, the material to be infused is a polymer. In some embodiments where an infusing step is used, the material to be infused comprises a growth factor or antibiotic. In some embodiments where an infusing step is used, the material to be infused is selected from the group consisting of hydroxyapatite, fluoroapatite, chloroapatite, bromoapatite, iodoapatite, calcium sulfate, calcium phosphate, calcium carbonate, calcium tartarate, bioactive glass, and any combination thereof.

In another aspect of the present invention, there is a method of making a medical implant having a porous surface comprising the steps of placing a finite number of non-spherical individual bodies in continuous contact with one another; and, sintering said individual bodies by applying pulsed electrical energy across at least a portion of the aggregate mass of said individual bodies, thereby creating a cohesive porous structure. In some embodiments, the step of placing a finite number of non-spherical individual bodies in continuous contact with one another further comprises placing said individual bodies in contact with at least one plac other material. In some embodiments, the method further comprises the step of removing at least a portion of said at least one other material either during or after said step of sintering, thereby creating a cohesive porous structure where said material was removed. The method may further comprise the step of applying a mechanical load to at least a portion of said individual bodies. In some embodiments, the step of applying a mechanical load is performed during said step of sintering. In some embodiments, the step of sintering is performed at an elevated temperature. In some embodiments, the step of sintering comprises applying pulsed electrical energy at high frequencies. In some embodiments, the individual bodies are selected from the group consisting of metal, ceramic, polymer, composite materials, and any combination thereof. In some embodiments, the composition of a portion of the individual bodies is different from the composition of another portion of the individual bodies. In some embodiments, at least a portion of said individual bodies comprise a refractory material. In some embodiments, the individual bodies have a form selected from the group consisting of symmetric particles, asymmetric particles, single fibers, multiple fibers, flat porous sheets, deformed porous sheets, reticulated open-celled structures, and any combination thereof. In some embodiments, the sintering step is performed in a controlled environment. The controlled environment may be one having a pressure less than atmospheric pressure. The controlled environment may be one comprising an atmosphere of an inert gas. The controlled environment may be one comprising an atmosphere of a reactive gas. In some embodiments of the method, the controlled environment is varied during the step of sintering. In some embodiments, the step of placing comprises using a binder. In some embodiments, the method further comprises the step of infusing at least a portion of the porous structure with a material. In some embodiments, the step of infusing comprises infusing with a method selected from the group consisting of direct compression molding, injection, solution deposition, vapor deposition, and any combination thereof. In some embodiments where an infusing step is used, the material to be infused is a polymer. In some embodiments where an infusing step is used, the material to be infused comprises a growth factor or antibiotic. In some embodiments where an infusing step is used, the material to be infused is selected from the group consisting of hydroxyapatite, fluoroapatite, chloroapatite, bromoapatite, iodoapatite, calcium sulfate, calcium phosphate, calcium carbonate, calcium tartarate, bioactive glass, and any combination thereof.

The present invention also includes a medical implant comprising a solid substrate and a porous sintered surface, wherein the solid substrate possesses substantially the same bulk mechanical and tribological properties after sintering which existed prior to sintering. Preferably, the material possesses substantially the same microstructure after sintering which existed prior to sintering.

There is also a medical implant having a porous surface produced by the process comprising the steps of placing a finite number of non-spherical individual bodies in continuous contact with one another; and, sintering the individual bodies by applying pulsed electrical energy across at least a portion of the aggregate mass of the individual bodies, thereby creating a cohesive porous structure.

There is also a medical implant having a porous surface produced by the process comprising the steps of placing a finite number of individual bodies in continuous contact with one another, said finite number of individual bodies comprising a first material; sintering the first material by applying pulsed electrical energy across at least a portion of the aggregate mass of the individual bodies, thereby creating a cohesive porous structure; and, attaching the first material to a second material, the second material comprising said solid substrate.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

DETAILED DESCRIPTION OF THE INVENTION

Figure 1:
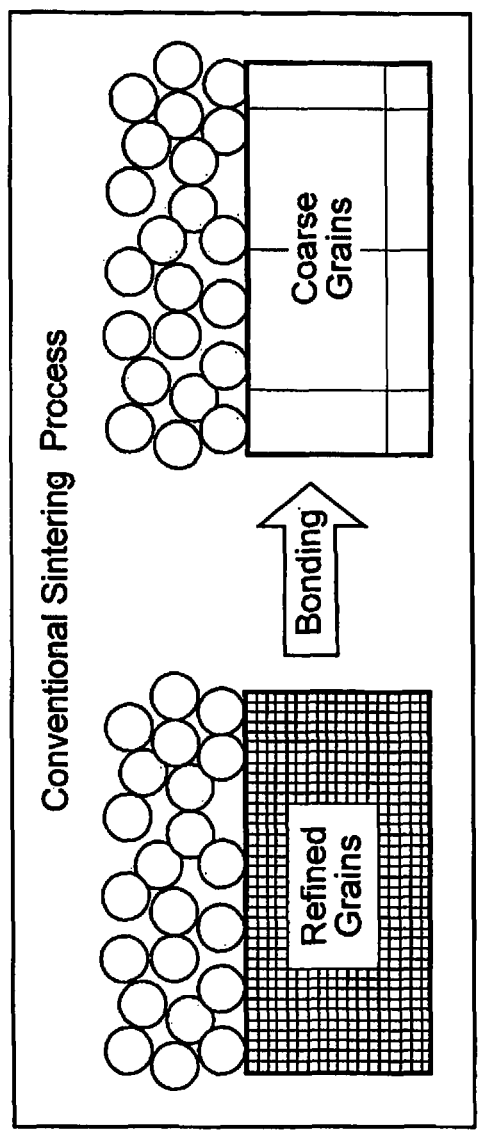
FIG. 1 is a demonstrating the result of the use of conventional sintering on an medical implant.

The present invention describes a medical implant and a method of making a medical implant comprising a porous surface for tissue ingrowth and ongrowth. Specifically, sintered medical implant product is described. The sintered product avoids the changes in bulk microstructure and the corresponding changes in the mechanical and tribological properties of a solid substrate which occurs when high temperature sintering is required to create and bond a porous tissue ingrowth and ongrowth surface to an implantable medical device.

As used herein, "a" or "an" is defined herein as one or more. Unless otherwise indicated or apparent by the context, the singular includes the plural and the plural includes the singular herein.

As used herein, "metal" means any material comprising a metal and includes, but is not limited to, metals and metal alloys.

As used herein, "non-refractory" means a material that melts at a relatively low temperature, typically, a temperature lower than that defined by the melting points of iron, cobalt and nickel.

As used herein, "refractory" means a material that melts at a high temperature, typically, a temperature higher than that defined by the melting points of iron, cobalt and nickel.

As used herein, "porous" means a material, or a portion thereof, having at least 20% surface-connected porosity with an average pore size ranging from about 10 microns to about 1000 microns. The term "porous" may connote regions within a material, i.e., a material may have regions of porosity while having other regions which are non-porous.

As used herein, "solid" means a material have less than 5% porosity.

As used herein, "tissue" means any and all bodily tissue, including bone and soft tissue.

Sintering is a simple process whereby particular material in powder form is heated to a high temperature less than the melting point, whereby the particles bond to each other, producing a porous (on a microscopic scale) material. These materials include but are not limited to, metals, metal alloys, and ceramics. Sintering is a method for making strong ceramic objects from ceramic powder. The process typically includes mixing water, binder, antiflocculant, and ceramic powder to form a slurry. The slurry is spray dried and put into a mold and pressing it to form a green body (an unsintered ceramic material) The green body is heated at low temperature to burn the binder off. The material is heated at high temperature (but lower than its melting point) to fuse the ceramic particles together. A similar process of sintering is sometimes used to form metallic objects. Sintered bronze in particular is frequently used as a material for bearings since it is porous and thus allows lubricants to flow through. The result is a fairly low density material which can be cut and shaped fairly easily, can hold small loads in compression, and provides good thermal insulation, but cannot take much stress in tension and is brittle. Sintering allows production of parts without melting and liquid casting processes, i.e., dealing with only powder or fine sand. Sintering is the most common technique for consolidating powders.

Sintering techniques have been used to produce porous surfaces for medical implants. The porous surfaces of such implants exhibit excellent tissue ingrowth and ongrowth properties. However, conventional sintering methods result in degradation in mechanical and tribological properties. Attempts to address this problem in the prior art have focused on the use of alternative, less desirable porous surfaces, and the use of sintering aides to attempt to decrease the sintering temperatures and lessen the changes to the microstructure of the bulk of the material. In the context used herein, the surface of the implant materials extends to a first approximation to about one micron. The bulk exists at deeper levels.

There are many methods for sintering a component. The most important are: vapor-phase sintering; solid-state sintering; liquid-phase sintering; reactive liquid sintering. Overpressure sintering uses pressure to accelerate densification. The biggest problem of this technique is shrinkage which causes cracking and distortion. Importantly, where sintering is used to create a porous surface on a substrate, the somewhat harsh conditions necessary for sintering result in unwanted changes in the substrate material for given applications.

The inventors have found that sintering methods which utilize pulsed electrical current to effect a substantially localized heating of the interfaces between portions of material to be sintered result in a superior sintered device for medical implant applications. While heating may not be completely limited to these interfaces, it is at least kept to a minimum in other regions. Implants produced using pulsed current techniques can produce strongly bonded porous surfaces while maintaining or only minimally changing the microstructure of other material regions of the implant. Sintering techniques which utilize the application of pulsed electrical energy are known by a variety of names, including spark plasma sintering (SPS), pulsed electric current sintering (PECS), and field activated sintering technique (FAST). In this general technique, it is possible to produce high quality sintered materials in short periods by charging the intervals between powder particles (or other material forms) with electrical energy and, in some cases, a high mechanical load between the materials to be sintered.

In pulsed current sintering, sufficient current is supplied such that electrical arcing occurs across interfaces, especially the spaces between portions of the material(s) to be sintered. The interfacial resistivity causes a localized heating to occur. Such heating is localized to the spaces between portions and the surfaces of the material portion. It is possible to use this technique and minimize the more general resistive heating (Joule heating) that occurs in the bulk of the material. It is this latter form of heating which modifies the bulk of the material in unwanted ways, including, but not limited to, grain growth in the bulk of the material. In this technique, small particles or beads are preferred. A finite number of such bodies are placed in continuous contact with one another and a pulse of electrical energy is applied across at least a portion of the aggregate mass of the bodies. A localized heating occurs at the contact areas between the bodies, resulting in their union at the contact points. The resulting structure is porous. The bodies can be sintered to one another and/or to a solid substrate material.

In the present invention, the thermal energy so transferred to the material is ideally just enough to cause bonding of the material. Any excess energy should be minimized, as such energy will contribute to further heating of the bulk and potentially affect the bulk microstructure. Sintering with pulsed electrical energy allows one to achieve or approximate this condition of energy transfer if sintering is performed under appropriate conditions. The frequency of the electrical pulse is one parameter which may be manipulated to achieve this result. By increasing the frequency of the pulse, the result will be to drive the current to the surface. The current under these conditions skims the surface and will effect the desired bonding to form a porous surface. Accordingly, high frequencies are preferred. A pulse rate of at least 1 pulse per second is preferred, although lower frequencies may be acceptable for particular applications. More preferably, much higher pulse rates are desired, on the order of 10 pulses/second (10 Hz) to 1 pulse/microsecond (1 MHz) and higher. Frequencies of 10 pulses/second and above are considered high frequencies herein. The time between pulses may, but need not, be equal to the time duration of an individual pulse. The asymmetry may favor either the "on" time or the "off" time. These parameters, like all others in pulsed current sintering of medical implants, may be varied to best suit the materials being used to fabricate the implant.

Another parameter which can be controlled to effect a more localized heating of the surface as opposed to a general heating of the surface and bulk, is to accelerate the bonding process. The shorter the duration of the application of thermal energy to the implant, the less will be the change in the microstructure of the bulk of the material. This may be accomplished, for example, by applying and/or increasing the mechanical load on the implant. This forces the particles to be bound more closely together. This hastens the bonding and permits the process to be completed with the addition of a minimum of electrical (and therefore, thermal) energy.

In one embodiment of the present invention, the material is placed in an graphite tube housing ("outer die") with two graphite plugs on either end of the tube. The outer die, or "tube housing" as stated here, could also be made from other materials. For example it could be made of a non-conductive material, such as a ceramic. Having a graphite die allows some of the current to be used to heat the die (through resistive or Joule heating). With a non-conductive die, more of the current would go through the sample itself. However, graphite also has a higher thermal conductivity, and can remove heat from the sample more quickly than a ceramic. Electrodes which are used to apply the pulsed current must always be conductive. In the case of a sintered surface on a solid substrate, the surface material is placed in contact with the substrate, either with or without a binder material. It is important that the graphite plugs, or other conductive material, contact the material(s) to be sintered. Electrodes contact the material such that a pulsed current may be applied. The current pulses travel through the material and arc across gaps in the material. These gaps are most often the spaces between the material to be sintered. The current encounters resistance at these interfaces. This interfacial resistance causes a localized heating where it occurs.

In the basic method, a first material is sintered by electrically charging it with pulsed electrical energy. The electrical energy is pulsed at high frequencies, preferably greater than 1 pulse per second, and preferable, the material is under a mechanical load. Preferably, when a mechanical load is used, it is a compressive load of at least 1 N. The magnitude of the pulse can be varied as well to optimize results. Conditions are optimized when sintering occurs and the microstructure of the subsurface bulk of the material is not changed or is not substantially changed from that which existed prior to the application of the pulsed electrical energy. Most preferably, the absence of a change in microstructure is evidenced by no grain growth or by substantially no grain growth or when there is no change or substantially no change in the distribution of any of the component phases in the subsurface bulk of the material after application of the pulsed electrical energy when compared to that which existed before application of the pulsed electrical energy. When so pulsing with electrical energy, the spaces between portions of the material are heated, and the heating being substantially localized to said spaces and to the surface of said portions.

In the case where a medical implant having a solid substrate and a porous surface is desired, a second material is used. The second material may be the same or different from the first material. In some cases, the second material may be electrically charged with pulsed electrical energy.

It may be preferable to perform the process at elevated temperatures. In this way, the material to be sintered required less electrical energy to reach the bonding energy. When elevated temperatures are used, they should be below those temperature which cause substantial change in the substrate microstructure (or a change in the microstructure of the subsurface bulk in the case of a free-standing porous implant).

As discussed above, efforts to improve medical implants by application of porous surfaces has found limited success but improvements are needed. Conventional sintering techniques have been used, but the conditions necessary for conventional sintering techniques have unwanted effects on substrate materials that form the bulk of the implant. By using electrical sintering and maintaining the proper conditions, these unwanted effects may be reduced or eliminated, resulting in a superior porous medical implant.

Figure 2:
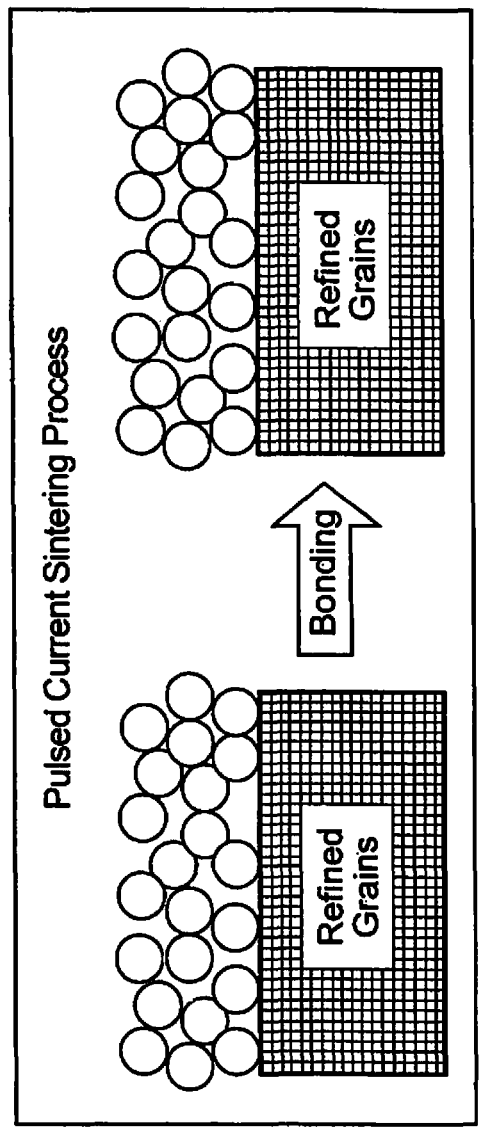
FIG. 2 is a schematic illustration demonstrating the result of the use of pulsed current sintering on an medical implant.

The inventors have applied this technology to the fabrication of medical implants with porous surfaces and have found that superior medical implants can be so made. By avoiding the high temperature sintering cycle required to bond most porous tissue ingrowth coatings, bonding can be achieved while maintaining a refined substrate microstructure, better preserving the original mechanical, tribological, and oxidation properties of the substrate. Microstructure and grain size in the substrate are unchanged or are substantially unchanged. This is schematically illustrated in FIGS. 1 and 2. FIG. 1 demonstrates the results of conventional sintering, while FIG. 2 demonstrates the results of pulsed current sintering. In some cases, bonding is achieved while maintaining an average final substrate grain size of less than 1 mm. Also, since this process is less dependent on differences in melting points, it is possible to join refractory and non-refractory materials without the use of an intermediate layer to enhance or enable bonding. Although FIGS. 1 and 2 demonstrate the preservation of the mechanical and tribological properties of the substrate before and after pulse electrical sintering, the same can also be said for the bulk (i.e., non-surface region) of the sintered bodies (depicted as the spheres in FIGS. 1 and 2). It is possible to preserve the mechanical and tribological properties of the bulk region of the sintered bodies also. Depending upon the conditions used, the surface areas of the sintered bodies (particularly those areas in physical contact with other surfaces) may experience a significant change in mechanical and tribological properties. Changes in mechanical and tribological properties are typically manifest by a change in microstructure such as a change in grain size or an altered distribution of crystal phases, and/or other properties. Such changes are often deleterious to the performance of medical implants. Thus, avoiding these changes will lead to improved implants.

Another advantage of the pulsed electrical sintering method is that non-spherical particles can be used to produce an equally strong, but more porous structure. Packed spherical particles of uniform size typically produce a porosity of only 25-35%. The packing density of uniformly-sized non-spherical particles can produce much greater porosity, which is desirable for stand-alone porous implants. However, in conventional sintering, irregular particles, for example, typically have fewer and smaller necking regions, or regions where the particles sinter together, giving irregular particle porous coatings lower attachment strength than spherical particle porous coatings. Increasing the sintering temperature or applying pressure during sintering could increase bonding strength of irregular powder porous coatings, however both methods are likely to have detrimental consequences. For example, either method increases the likelihood of collapse of the porous structure being sought. Furthermore, if being bonded to a solid substrate, increasing the sintering temperature increases the likelihood that the substrate microstructure will be detrimentally affected. Spherical bodies would normally be preferred because they are inherently self-supporting, reducing the likelihood of collapse of the porous structure, and pack more uniformly and repeatably than non-spherical bodies, particularly under the mechanical loads preferred by this method, resulting in greater porosity and a more regular and uniform distribution of porosity of the resulting sintered product. The inventors have found that the sintering performance of non-spherical particles is much improved in pulsed electrical sintering in comparison to conventional sintering. As a result, medical implants can more readily be made non-spherical bodies using pulsed electrical sintering.

The medical device is made by bonding or simultaneously creating and bonding a metallic, ceramic, polymer, or composite porous structure to a solid metallic, ceramic, polymer, or composite substrate using pulsed electrical sintering. The bonding in the device is achieved using pulsed electrical sintering in a vacuum or inert gas environment to prevent material/environment reactivity or to modify heat flow behavior. The bonding may be achieved using pulsed electrical sintering in combination with pressure and/or additional heat. In the fabrication of the device, a porous surface can be created with lower temperatures and/or pressures than traditional sintering or diffusion bonding methods used for medical implants.

In a preferred embodiment, the medical implant comprises a solid substrate and a porous sintered surface. The solid substrate and porous surface may be composed of substantially the same material(s). For example, titanium metal or titanium metal alloy may be sintered onto a titanium or titanium alloy surface. Alternatively, they may be composed of substantially different materials. For example, titanium may be sintered onto a cobalt-chromium surface, or a metal or metal alloy may be sintered onto a ceramic surface. Alternatively, the medical implant may comprise a purely porous component. In either case, the medical implant may comprise a variety of materials, including but not limited to, metal, ceramic, polymer, composite materials, and any combination thereof. The present invention is applicable to all conventional implant materials. The material and their precursors may have a variety of forms, including but not limited to, particles, fibers, flat porous sheets, deformed porous sheets, reticulated open-celled structures, and any combination thereof. Where the medical implant comprises more than one material, the materials may be the same or different (for example, both may be titanium or a titanium alloy). Additionally, where the medical implant comprises more than one material, the materials may have the same or different forms (e.g., particles, fibers, etc.). In some applications, the final medical implant may comprise bioactive ceramic materials such as hydroxyapatite, fluoroapatite, chloroapatite, bromoapatite, iodoapatite, calcium sulfate, calcium phosphate, calcium carbonate, calcium tartarate, bioactive glass, and combinations thereof.

To fabricate the implant, a first material is sintered by electrically charging it with pulsed electrical energy under conditions in which spaces between portions of it are heated. As a result, the heating is substantially localized to said spaces and to the surface of said portions. The first material is then attached to a second material. The second material is preferably a solid substrate. It should be noted that the attachment may occur as a consequence of the sintering step in some cases. In such cases, the sintering of the first and second materials may occur simultaneously to the sintering of the bodies of the first material (for example, wherein the pulsed electrical energy sinters the bodies of the first material to each other and to the second material. Alternatively, sequential sintering steps may be used. In other cases, the sintered material may be attached to the substrate by some other means. This may be accomplished by any of the various ways known to those of skill in the art, including but not limited to, diffusion boding, welding, soldering, brazing, attaching with adhesive or grouting material, or any combination thereof, etc. The first and second materials may be the same or different, both in terms of composition and properties. Each material, whether it be the first material, the second material, or any other material(s), may be a pure material, or it may comprise a mixture. In other words, each material, as that term is used herein, may comprise one or more than one material. The term "material" includes both the singular and the plural. This is true for all embodiments of the present invention.

The implant may have a porous structure made from a refractory material and a substrate made from a non-refractory material. The implant may have a porous structure made from a non-refractory material and a substrate made from a refractory material. In the case where the medical implant comprises a purely porous component (e.g., a stand alone porous structure without a solid substrate), it may be made of a refractory material, a non-refractory material, or both.

Creating the porous surface is accomplished by sintering a precursor material. The form of the porous structure precursor may vary in the present invention. The porous structure precursor may be any of a number of different forms. These include, but are not limited to, beads, particles, single or multiple fibers, flat or deformed porous sheets, reticulated open-celled structures, and others. The beads and particles may be of any shape and form, such as spherical or non-spherical, symmetric or asymmetric. Combinations of any of these forms are also possible. The porous structure precursor may be comprised of a variety of materials, including, but not limited to, metals, ceramics, polymers, and composite materials. Combinations of any of these materials are also possible.

In some embodiments, the porous structure precursor is temporarily attached or positioned to the substrate using a binder. The binder could be cellulose or other commonly used binders in the sintering field. Wax may be used in some cases. In some cases, the porous structure is created by the removal of an interconnected pore-creating secondary material during or after the bonding process.

Although use of the present invention allows for the production of a substrate material directly bonded to a porous surface, it is also within the scope of the invention to produce a stand-alone porous structure with the pulsed current techniques herein described and bond that structure to a substrate using an intermediate bonding layer. Bonding in the present invention may be achieved without the use of an intermediate layer whose main purpose is to enhance or enable bonding. Such structures and methods of making them are known in the art, e.g., see U.S. Published Application No. 2003/0232124 to Medlin et al.; U.S. Pat. No. 6,063,442 to Cohen et al. Boron-containing compounds may also be an intermediate layers with nickel-based metals. Stand-alone porous structures without a bound substrate may also be produced. These are useful in particular applications as medical implants.

The basic method may also be modified to include the use of a pore-creating material. The pore-creating material may be mixed or otherwise combined with the implant materials. The pore-creating material can be any volatile, dissolvable, and/or decomposable material. The pore-creating material forms a matrix with the implant material and is subsequently removed by decomposition, volatilization, dissolution, any combination thereof, etc. Examples included titanium hydride, which decomposes through loss of the hydride hydrogen; naphthalene, which is removed through sublimation; and various salts, which may be washed out of the matrix.

Where desirable, the methodology can be used to produce a medical device in which the same or different morphologies are bonded to different regions of the device. The use of different surface morphologies enables optimization of the surface for interaction with certain types of tissue. The medical device may be manufactured such that different portions of it are optimized for specific ingrowth results. For example, the device can be fabricated such that at least one region is intended for soft/fibrous tissue ingrowth, while at least one region is intended for bone tissue ingrowth. In another embodiment, the medical implant is infused with ultra-high molecular weight polyethylene or other load-bearing implantable polymers. Typically, this is done through a direct compression molding process and at least one region is intended for bone or soft/fibrous tissue ingrowth. Other possible methods to infuse, include, but are not limited to, solution deposition, vapor deposition, or various injection techniques such as injection molding or injection of a curable polymer. The medical implant may also be infused with other active biomolecules such as growth factors or drugs such as antibiotics. These materials may be infused into the medical implant in a polymer matrix which may be infused as discussed above or by other means.

The process for creating the porous surface is pulsed electrical sintering. As discussed above, the technique uses a pulsed frequency current to create a localized heating that results in sintering without significant perturbation of the substrate phase. The process may comprise the bonding of multiple substrate surfaces simultaneously. The process may comprise bonding surfaces that are non-planar, such as an acetabular shell or a hip stem. The process may comprise two or more non-coplanar substrate surfaces simultaneously, for example, two or more of the fixation surfaces of a knee femoral component.

The invention also includes a medical implant made by bonding together metallic, ceramic, polymer, or composite non-spherical particles, fibers, or flat or deformed porous sheets using pulsed current sintering. In some cases, the particles, fibers, or sheets of the device are comprised of substantially the same materials. Alternatively, the particles, fibers, or sheets of the device are comprised of two or more substantially different materials. In the case of different materials, the combination of materials may be chosen such that at least one material provides enhanced mechanical properties and at least one material provides enhanced tissue ingrowth properties. The medical implants of the present invention include those that incorporate only particles, fibers, or sheets, or any combination of particles, fibers, or sheets. Alternatively, the medical device incorporates spherical beads with any combination of particles, fibers, and sheets.

Implants which have regions of porosity and non-porous regions are also possible. The different regions may have different characteristics also. For example, the medical implant may have comprise a titanium alloy substrate with a porous region having sintered titanium and another porous regions with sintered zirconium. Medical implants having other final constructions are possible. For example, the present invention includes an implant having porous regions sandwiched between solid substrates and vice versa.

Additionally, implants which possess porosity everywhere, instead of those having a porous surface on a solid substrate are within the scope of the present invention. Purely porous implants formed by pulsed current sintering have the advantage of a more refined subsurface bulk.

The present invention is applicable to all medical implants. However, its most important application is expected to be in the area of joint prostheses and other orthopaedic implants. For example, fixation stability is a common problem for hip and knee prostheses. Other applications include but are not limited to shoulder, elbow, ankle, finger, wrist, and toe prostheses. The ability to produce a stable, porous surface for tissue ingrowth and ongrowth, while preserving the integrity of the bulk will lead to a superior prosthesis. The invention is applicable to other joint prostheses as well, including, but not limited to, shoulder and elbow prostheses. Other medical implants that can be improved through the use of the invention include vertebral implants and dental implants. Also, the present invention can be applied to maxillofacial and tempromandibular implants. It can also be applied to bone implant hardware, including, but not limited to, nails, screws, rods, pins, plates, spacers, wedges, void fillers, and any combination thereof.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps. All patents and patent applications cited herein are incorporated by reference as though fully set out herein.

What is claimed is:

1. A method of making a medical implant having a porous surface and a solid substrate, comprising the steps of:
    placing a finite number of individual metallic bodies in continuous contact with one another at a first interface, said finite number of individual metallic bodies comprising a first material;
    sintering said first material at the first interface by applying pulsed electrical energy across at least a portion of the aggregate mass of said individual metallic bodies, thereby creating a cohesive porous structure;
    placing the sintered first material in continuous contact with a second material at a second interface, said second material comprising a solid metallic substrate; and
    sintering said first material to the second material at the second interface by applying pulsed electrical energy across at least a portion of the aggregate mass of the first material and the second material;
    wherein the solid substrate possesses substantially the same bulk mechanical and tribological properties after the act of attaching the first material to the solid substrate as existed prior to the act of attaching the first material to the solid substrate.

2. The method of claim 1, wherein said steps of sintering are performed simultaneously by applying pulsed electrical energy across at least a portion of the aggregate mass of the first material and the second material while the first material and the second material are in physical contact with one another.

3. The method of claim 1, wherein said steps of sintering are performed sequentially by first applying pulsed electrical energy across at least a portion of the aggregate mass of the first material and thereafter applying pulsed electrical energy across at least a portion of the aggregate mass of the first material and the second material while the first material and the second material are in physical contact with one another.

4. The method of claim 1, wherein said step of placing a finite number of individual metallic bodies in continuous contact with one another comprises placing a finite number of individual bodies of at least two metallic materials in continuous contact with one another.

5. The method of claim 4, further comprising the step of removing at least a portion of at least one of said at least two materials either during or after said step of sintering, thereby creating a cohesive porous structure where said material was removed.

6. The method of claim 1, further comprising the step of applying a mechanical load to at least a portion of said first material or to at least a portion of said second material or to at least a portion of both said first material and said second material.

7. The method of claim 6, wherein said step of applying a mechanical load is performed during said step of sintering.

8. The method of claim 1, wherein said step of sintering is performed at an elevated temperature.

9. The method of claim 1, wherein said step of sintering comprises applying pulsed electrical energy at high frequencies.

10. The method of claim 1, wherein the composition of said first material and said second material are different.

11. The method of claim 1, wherein the first material and the second material are refractory materials.

12. The method of claim 1, wherein one or both of the first material and the second material are non-refractory materials.

13. The method of claim 1, wherein a portion of said individual bodies of said first material are of different composition from another portion of said individual bodies of said first material.

14. The method of claim 1, wherein a portion of said individual bodies of said first material comprises a refractory material and another portion of said individual bodies of said first material comprises a non-refractory material.

15. The method of claim 1, wherein one of said first material and said second material is refractory and the other is non-refractory.

16. The method of claim 1, wherein said first material has a form selected from the group consisting of symmetric particles, asymmetric particles, single fibers, multiple fibers, flat porous sheets, deformed porous sheets, reticulated open-celled structures, and any combination thereof.

17. The method of claim 16, wherein said first material has a symmetric particle form and is a spherical particle.

18. The method of claim 1, wherein said step of sintering is performed in a controlled environment.

19. The method of claim 18, wherein said controlled environment is a pressure less than atmospheric pressure.

20. The method of claim 18, wherein said controlled environment comprises an atmosphere of an inert gas.

21. The method of claim 18, wherein said controlled environment comprises an atmosphere of a reactive gas.

22. The method of claim 18, wherein said controlled environment is varied during said step of sintering.

23. The method of claim 1, wherein said step of placing comprises using a binder.

24. The method of claim 1, further comprising the step of infusing at least a portion of the porous region with a material.

25. The method of claim 24, wherein said step of infusing comprises infusing with a method selected from the group consisting of direct compression molding, injection, solution deposition, vapor deposition, and any combination thereof.

26. The method of claim 24, wherein said material to be infused is a polymer.

27. The method of claim 24, wherein said material to be infused comprises a growth factor or antibiotic.

28. The method of claim 24, wherein said material to be infused is selected from the group consisting of hydroxyapatite, fluoroapatite, chloroapatite, bromoapatite, iodoapatite, calcium sulfate, calcium phosphate, calcium carbonate, calcium tartarate, bioactive glass, and any combination thereof.

29. The method of claim 1 wherein the substantially same bulk mechanical and tribological properties possessed after the act of attaching the first material to the solid substrate include average grain size of the solid substrate.

30. The method of claim 1 wherein the substantially same bulk mechanical and tribological properties possessed after the act of attaching the first material to the solid substrate include microstructure of the solid substrate.

31. A method of making a medical implant having a porous surface comprising the steps of:
placing a finite number of non-spherical individual metallic bodies in continuous contact with one another at a first interface;
placing at least a portion of the finite number of non-spherical individual metallic bodies in contact with a solid metallic substrate at a second interface; and
sintering said individual metallic bodies to one another and at least in part to the solid metallic substrate at the first and second interfaces by applying pulsed electrical energy across at least a portion of the aggregate mass of said individual metallic bodies and the solid metallic substrate, thereby creating a cohesive porous structure on the solid metallic substrate;
wherein the solid metallic substrate possesses substantially the same bulk mechanical and tribological properties after the act of applying pulsed electrical energy as existed prior to the act of applying pulsed electrical energy.

32. The method of claim 31, wherein said step of placing a finite number of non-spherical individual bodies in continuous contact with one another further comprises placing said individual bodies in contact with at least one other material.

33. The method of claim 32, further comprising the step of removing at least a portion of said at least one other material either during or after said step of sintering, thereby creating a cohesive porous structure where said material was removed.

34. The method of claim 31, further comprising the step of applying a mechanical load to at least a portion of said individual bodies.

35. The method of claim 34, wherein said step of applying a mechanical load is performed during said step of sintering.

36. The method of claim 31, wherein said step of sintering is performed at an elevated temperature.

37. The method of claim 31, wherein said step of sintering comprises applying pulsed electrical energy at high frequencies.

38. The method of claim 31, wherein the composition of a portion of said individual bodies is different from the composition of another portion of said individual bodies.

39. The method of claim 31, wherein at least a portion of said individual bodies comprise a refractory material.

40. The method of claim 31, wherein said individual bodies have a form selected from the group consisting of symmetric particles, asymmetric particles, single fibers, multiple fibers, flat porous sheets, deformed porous sheets, reticulated open-celled structures, and any combination thereof.

41. The method of claim 31, wherein said step of sintering is performed in a controlled environment.

42. The method of claim 41, wherein said controlled environment is a pressure less than atmospheric pressure.

43. The method of claim 41, wherein said controlled environment comprises an atmosphere of an inert gas.

44. The method of claim 41, wherein said controlled environment comprises an atmosphere of a reactive gas.

45. The method of claim 41, wherein said controlled environment is varied during said step of sintering.

46. The method of claim 31, wherein said step of placing comprises using a binder.

47. The method of claim 31, further comprising the step of infusing at least a portion of the porous structure with a material.

48. The method of claim 47, wherein said step of infusing comprises infusing with a method selected from the group consisting of direct compression molding, injection, solution deposition, vapor deposition, and any combination thereof.

49. The method of claim 47, wherein said material to be infused is a polymer.

50. The method of claim 47, wherein said material to be infused comprises a growth factor or antibiotic.

51. The method of claim 47, wherein said material to be infused is selected from the group consisting of hydroxyapatite, fluoroapatite, chloroapatite, bromoapatite, iodoapatite, calcium sulfate, calcium phosphate, calcium carbonate, calcium tartarate, bioactive glass, and any combination thereof.

52. The method of claim 31 wherein the substantially same bulk mechanical and tribological properties possessed after the act of applying pulsed electrical energy include average grain size of the solid substrate.

53. The method of claim 31 wherein the substantially same bulk mechanical and tribological properties possessed after the act of applying pulsed electrical energy include microstructure of the solid substrate.

* * * * *